United States Patent [19]
Adamyan et al.

[11] Patent Number: 6,086,578
[45] Date of Patent: Jul. 11, 2000

[54] METHOD FOR SKIN REJUVENATION

[75] Inventors: Arnold Aramovich Adamyan, Moscow; Vladimir Vasilyevich Lantukh, Novosibirsk; Olga Yuryevna Tsukanova, Moscow, all of Russian Federation

[73] Assignee: Zakrytoye Aktsionernoye Obschesto "Ostmedkonsalt", Moscow, Russian Federation

[21] Appl. No.: 09/342,095

[22] Filed: Jun. 29, 1999

[30] Foreign Application Priority Data

Dec. 17, 1998 [RU] Russian Federation ............. 98122435

[51] Int. Cl.[7] .......................... A61B 19/00; A61B 17/00; A61B 17/06
[52] U.S. Cl. .................. 606/1; 128/898; 606/204.35; 606/224; 606/230
[58] Field of Search ................. 128/898; 606/1, 606/204.35, 230, 224; 424/426

[56] References Cited

U.S. PATENT DOCUMENTS

| | | | |
|---|---|---|---|
| 2,153,889 | 4/1939 | Hames | 128/1.1 |
| 2,928,395 | 3/1960 | Forbes et al. | 128/335.5 |
| 3,867,190 | 2/1975 | Schmitt et al. | 117/138.8 |
| 3,942,532 | 3/1976 | Hunter et al. | 128/335.5 |
| 4,603,146 | 7/1986 | Kligman | 514/559 |
| 4,606,354 | 8/1986 | Jacob | 128/784 |
| 5,397,352 | 3/1995 | Burres | 623/11 |
| 5,713,375 | 2/1998 | McAllister | 128/898 |
| 5,854,382 | 12/1998 | Loomis | 528/354 |
| 5,902,599 | 5/1999 | Anseth et al. | 424/426 |

OTHER PUBLICATIONS http://www.botanical.com/botanical/mgmh/g/golthr25.html, Oct. 18, 1999.

Frishberg I.A., Cosmetic Facial Operations, Moscow, 1984, pp. 182–185.

Rees T.D., Plastic Reconstruction Surgery of the Face and Neck, 1977, vol. 1, "Silicone Injection Therapy . . . ", pp. 247–250.

*Primary Examiner*—Linda C. M. Dvorak
*Assistant Examiner*—Jocelyn Debra Ram
*Attorney, Agent, or Firm*—Jacobson, Price, Holman & Stern, PLLC

[57] ABSTRACT

A rejuvenation method includes subcutaneous implanting an inert material at the rejuvenation area. Golden threads are used as the inert material. The golden threads are implanted in subdermal space at the level of the derma inner edge. The golden threads are implanted along and/or across wrinkles and skin folds of the rejuvenation area catching skin regions behind the rejuvenation area. The golden thread input and output sites are placed in skin regions located behind the rejuvenation area. The skin is first marked with marker lines the length of which is greater than the rejuvenation area, and the inert material is implanted under these lines. The marker lines may be applied so as to intersect and to form a net. The golden thread input and output sites are placed in site of intersection of the marker lines forming the net. The golden thread is employed in conjunction with a resolving polyglycol thread. Rejuvenation is applied to skin areas on cheeks, chin, near eyes, on arms and/or thighs.

10 Claims, No Drawings

METHOD FOR SKIN REJUVENATION

This patented invention relates to plastic (aesthetic) surgery and can be used to rejuvenate human skin, especially the skin located on the face, neck, arms and thighs.

One method for skin rejuvenation is the surgical removal of wrinkles on the face and neck by circular skin tightening. The skin is incised from the temporal area and the incision descends around the ear lobe. This incision continues in the postaural fold to the neck. Additional skin peeling is performed. Finally, the skin is tightened and the excess is cut off (Frishberg I.A., Cosmetic Facial Operations, Moscow, 1984, pp. 182–185).

The disadvantages of this procedure are the high trauma, and the high risk of post-operation side effects such as hematomas and scar complications. The circular tightening mechanically stretches the wrinkles but does not affect the structure and the healthy condition of the skin.

Another method for restoring aged skin removes facial wrinkles by epidermatically introducing Vitamin A acid (see U.S. Pat. No. 4,603,146, C1-A 61 K 31/20, published 1986).

The drawbacks of this method are the low efficiency and low duration of the rejuvenation process.

Another method for smoothing facial folds and wrinkles utilizes the subcutaneous introduction of dermal autotransplants into a specifically formed pocket in the skin (see U.S. Pat. No. 5,397,352 C1-A 61 F 2/02, published 1995).

The drawbacks to this method are trauma and low efficiency. Shortly after the procedure, the implanted areas decrease and the skin folds appear again.

Another method for skin rejuvenation utilizes the subcutaneous implantation into the desired area of an inert material consisting of liquid silicone. Rees T. D., Plastic Reconstruction Surgery of the Face and Neck, 1977, volume 1, "Silicone Injection therapy in Atrophy of the Face", pgs. 247–250.

There are several disadvantages to this particular procedure which include:

Low efficiency due to a rapid migration into adjacent tissue

Reduction in volume

Slacking

Post-operational after-effects including non-specific inflammation and allergic reactions Silicone fails to provide a prolonged and stable cosmetic effect.

The goal of this patented invention is to increase the efficiency and reduce the post-operational side effects.

The above results are achieved because the skin rejuvenation process is comprised of the subcutaneous implantation of an inert material on the rejuvenation area. Unlike the prior method used in wrinkle reduction, the inert material is comprised of golden(Au)threads implanted into the subdermal space.

These results are also achieved by implanting the golden threads along and/or across wrinkles or skin folds found in the specific rejuvenation area. The golden threads are implanted in a way so they catch skin areas located behind a specific rejuvenation area. The input and output sites of the golden threads are the intersection points of vertical and horizontal lines (forming a grid or net) drawn across the rejuvenation area. The length of these lines is longer than the wrinkles found in the rejuvenation area. The golden threads are used in conjunction with a resolving polyglycol thread. Both the golden threads and the polyglycol threads are attached to a needle. The distance between an input site and an output site for the golden thread is longer than the length of the needle used to implant the thread. This method can be used to rejuvenate areas of skin located on the face, chin, neck, arms and/or thighs.

The patented method consists of the following procedure:

The area to be rejuvenated is pre-treated with antiseptic and lines are drawn across the rejuvenation area. The inert material is then implanted under these lines. The implants consist of a fragile, easily broken golden thread. To prevent the golden thread from breaking during the implantation process, it can be used in conjunction with a resolving, polyglycol thread whose purpose is to sustain the tension during the implantation process.

The golden threads are implanted along and across wrinkles in the rejuvenation area and secured to skin areas located behind the rejuvenation area.

To facilitate the implantation process, the skin is marked with lines, 25 cm in length, drawn with a marker. The lines are applied to areas of skin located on the face and body where both wrinkles and reduced skin tone and elasticity are present. On the face, these areas are the cheeks, the forehead, the temporal regions and the chin. On the body, these areas are the front of the neck, the inner and outer areas of the arms, the thighs, the breasts and the stomach. The lines are drawn so that they overlap the wrinkles. The lines are drawn longer than the length of the wrinkles and begin and end on areas of healthy skin. The number of lines depends on the individual characteristics of the patient's skin.

The golden threads are implanted under the wrinkled skin and in the direction of the wrinkles. To correct larger areas of skin containing small wrinkles and sags, the golden threads are implanted in a crosshatched (net) pattern along lines drawn across the rejuvenation area, which intersect each other.

A special needle, 6 cm in length, having a triple-edged sharpened point to which both the golden thread and the polyglycon thread are attached is inserted under the skin at the beginning of the marker line (the puncture site). The needle is pulled along the inner edge of the derma (under the skin) and is pulled out of the skin at the end of the marker line (the prick-out site). To prevent the ends of the thread from coming out of the skin surface when the needle is inserted into the skin, the end of the thread is pressed by a finger. The needle is then folded onto the thread tightening and secures it. When the needle is pulled out of the skin, the outcoming tip of the thread is pressed against the skin with scissors and then cut off. The design of the needle allows it to part the skin tissue without puncturing it, thus the skin is not traumatized. Both ends of the golden thread remain under the skin surface. The thread acts like a subcutaneous stitch, which is longer than the length of the needle.

The next step of the procedure is wrinkle-correction by the subcutaneous implantation of biogel. Biopolymeric gel is predominantly introduced into the areas of the face and body, which are difficult to access for golden thread implantation. It is also used to correct very deep wrinkles. On the face, these areas include the bridge of the nose, the temporal areas, the nasolabial folds, the "crow's feet" around the eyes, the upper and the lower lip zones, the corners of the mouth and the chin. The biopolymeric gel is introduced intracutaneously into the lower one-third of the derma, in a longitudinal direction along the length of the wrinkle as well as transversally to bind them. In order to induce correction of wrinkles, 2.5 to 6.5 ml of the biopolymeric gel is required. The gel consists of polydimethylsiloxane liquid with a viscosity of 350 to 360 centistokes.

Reduced trauma is a result because the puncture and the prick-out points for the golden threads and the biopolymeric gel are placed at the intersections of the marker lines due to the convergence of the needle input in different directions at a single point.

After the procedure, a sterile plaster is applied to all the puncture and prick-out sites for 12 to 24 hours. Within 5 to 6 days an anti-inflammatory ointment is applied to the injection regions.

The length of the golden thread is approximately 25 cm and the length of the needle is 6 cm.

The skin rejuvenation mechanism consists of the following:

The facial skin contains a large number of blood vessels, oil, and perspiration glands and nerve terminals. The action of enzymes, vitamins and hormones among these causes a reparative oxidation-reduction process to occur.

Upon implanting the golden threads into the subdermal space, a sharp metabolic and reparative process around the implant and polyglycol begins.

The polyglycol thread dissolves in two months due to a hydrolysis reaction to water. A protective cellular membrane forms around the golden thread causing an increased influx of blood. The tissue becomes rich in both oxygen and nutrients supplied by the increased blood supply. Because these newly formed cells have a more organized structure rich in vitamins, moisture, collagen and elastin, the exterior skin above the membrane rejuvenates. The golden threads are thinner than human hair and thus are not felt under the skin and do not hinder mimic movements.

Golden thread implants enhance the cosmetic effect of rejuvenation of the skin. They do not cause toxic or allergic reaction and because they are inert (chemically neutral) they are harmless to living tissue.

Subcutaneous golden thread implantation results in the stimulation of cell fibroblast proliferation and promotes collagen and elastin production. The new elastin tissue provides a tightening effect and enhances skin tone and elasticity. This effect is noticeable after only 1 to 1.5 months and the effects last 5 to 10 years.

Biogel implantation allows the correction of wrinkles located in areas inaccessible for golden thread implantation. It also corrects larger wrinkles or folds in the skin. The combination of golden thread and biogel produces a qualitative synergetic effect of skin rejuvenation. The golden thread implants initiate natural skin rejuvenation and the biogel implants volumetrically fill and straighten skin folds and wrinkles. The two implants thus work together and reinforce the rejuvenation effects of each other.

The golden threads are implanted subdermatically at the interior edge of the derma while the biogel is implanted subepidermally into the lower third of the derma. This reduces post-operational side effects and provides durable and stable cosmetic effect.

Implanting the golden threads above the optimum level (into the derma) increases efficiency of wrinkle correction but may create scaring due to blood vessel and nerve ending trauma. Implanting the golden threads below the derma (into the subcutaneous cellular tissue) reduces scaring but also reduces efficiency in wrinkle correction.

The present invention is illustrated in the following examples:

A female, 48 years of age with deep facial wrinkles, was in the clinic. Her skin is dry, flabby and atonic. Turgor and skin elasticity are reduced. There are wrinkles on the forehead, the bridge of the nose, the outer eye area (wrinkles here are referred to as "crow's feet"), over the upper lip and the corners of the mouth, on the nasolabial folds, and droops in the jugularmandibular zone of the neck.

Wrinkle reduction and correction was performed using the patented method described above. The rejuvenation area was treated with 0.5% chlorhexidine alcohol solution. Lines were drawn on the face and chin as guidelines for the golden thread implants. Local anaesthesia was performed using ultracaine. Golden threads were subdermatically implanted along four horizontal and five vertical stitches in the cheek region. The threads were implanted along the interior derma edge. The thread input and output sites were placed behind the rejuvenation area on adjacent skin regions.

Similarly, golden threads were implanted under the skin of the chin along four horizontal and six vertical stitches. All stitch lengths were longer than the wrinkles.

The next step was facial skin wrinkle correction by subepidermal injections of 4 ml of biogel. Plates of sterile plaster were applied to the input and output sites of the golden threads. The plates were removed after 24 hours and the face was antiseptically treated. The patient was given facial skin-care instructions and discharged from the clinic.

After 6 months, turgor and elasticity increased, wrinkles on the forehead, the bridge of the nose, around the eyes and in the nasolabial triangle zone were noticeably smoother. The skin in the jugular-mandibular zone tightened and lip volume increased. The skin appeared younger and healthier.

EXAMPLE 2

A female patient, age 42, was in the clinic for treatment of premature aging of skin located on the face and neck.

The skin was flabby, atonic and yellowish in color. The entire face is covered with a network of tiny wrinkles. There are marked skin folds on the forehead, neck and nasolabial folds.

Wrinkle reduction and correction was performed using the patented method described above.

The rejuvenation area was treated with 0.5% chlorhexidine alcohol solution. Three horizontal lines and four vertical lines were drawn on the face as guidelines for the golden thread implants. The golden threads were implanted subdermally along the interior edge of the derma under the lines drawn on the face. Similarly, golden threads were implanted under the skin of the chin along three horizontal and five vertical lines. Two additional stitches of golden threads, 25 cm in length, were implanted along two lines drawn on the edge of the lower jaw. The stitches of golden thread were longer than the wrinkle under which they were implanted.

Subsequently, golden threads were stitched along three horizontal lines and five vertical lines drawn on the front of the neck. Next, facial wrinkles were corrected by subdermally injecting 6 ml of biogel. Plates of sterile plaster were then applied to the sites of the golden thread implants. After 24 hours, the plates were removed and the face was treated antiseptically. The patient was given facial skin-care instructions and discharged from the clinic.

After four months, tugor and skin elasticity increased. Wrinkles on the forehead, the bridge of the nose, around the eyes and on the nasolabial triangle zone were smooth. Skin dryness disappeared and the skin tone improved. The woman appeared younger-looking.

This patented technique provides better results over the previous methods of wrinkle reduction:

post-operational side-effects are greatly reduced duration and stability of the cosmetic results last up to ten years skin structure and rejuvenation occur due to natural responses to the implanted golden threads and biogel postpones the need for surgical face lifts by 10 to 15 years This method has no counterindications, features simplicity and fewer traumas compared to surgical face lifting, peeling or dermobrasia and is successful in the treatment of aging skin.

What is claimed is:

1. A skin rejuvenation method providing the subcutaneous implantation of an inert material at a plurality of specific rejuvenation areas, comprising: implanting said inert material in a subdermal space, said inert material being a plurality of golden threads.

2. A method according to claim 1, wherein the golden threads are implanted along and/or across a plurality of wrinkles, where said wrinkles are skin folds of said specific rejuvenation areas.

3. A method according to claim 1, wherein there is a plurality of skin regions located behind one of the specific rejuvenation areas which are caught by the implantation of said golden threads.

4. A method according to claim 3, wherein an input site and an output site for the golden thread are both placed behind at least one of the specific rejuvenation areas.

5. A method according to claim 1, wherein one of the rejuvenation areas is first marked with a plurality of lines, the length of which is equal to, less than, or greater than at least one of the specific rejuvenation areas where the inert material is implanted.

6. A method according to claim 5, wherein the lines are drawn so that the lines intersect each other to form a grid or a net.

7. A method according to claim 6, wherein said input and output sites for the golden thread are located where the drawn lines forming the grid or net intersect each other.

8. A method according to claim 1, wherein the golden threads are used in conjunction with a resolving polyglycol thread, wherein both threads are attached to a needle.

9. A method according to claim 8, wherein a distance between a thread input site and a thread output site is greater than the length of the needle.

10. A method according to claim 9, wherein the rejuvenation areas for the implantation of the golden threads include areas of the face, chin, neck, arms, and/or thighs.

* * * * *